US008815158B2

(12) United States Patent
Zheng et al.

(10) Patent No.: US 8,815,158 B2
(45) Date of Patent: Aug. 26, 2014

(54) GRANULAR NANOPARTICLES HAVING BRIGHT FLUORESCENCE AND GIANT RAMAN ENHANCEMENTS

(75) Inventors: Jie Zheng, Somerville, MA (US); Xiaowei Zhuang, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 467 days.

(21) Appl. No.: 12/743,184

(22) PCT Filed: Nov. 14, 2008

(86) PCT No.: PCT/US2008/083560
§ 371 (c)(1),
(2), (4) Date: Oct. 19, 2010

(87) PCT Pub. No.: WO2009/064987
PCT Pub. Date: May 22, 2009

(65) Prior Publication Data
US 2011/0111518 A1 May 12, 2011

Related U.S. Application Data

(60) Provisional application No. 60/988,283, filed on Nov. 15, 2007.

(51) Int. Cl.
*G01N 21/64* (2006.01)
*G01N 21/65* (2006.01)
(52) U.S. Cl.
CPC .......... *G01N 21/6428* (2013.01); *G01N 21/658* (2013.01)
USPC ......... 422/82.07; 436/172; 424/489; 424/618
(58) Field of Classification Search
None
See application file for complete search history.

(56) References Cited

U.S. PATENT DOCUMENTS

| 2003/0068496 A1 | 4/2003 | Wei et al. |
| 2004/0229039 A1 | 11/2004 | Wei et al. |
| 2006/0115536 A1 | 6/2006 | Yacaman et al. |
| 2006/0147941 A1 | 7/2006 | Su |

FOREIGN PATENT DOCUMENTS

| WO | WO/9943427 A1 | 9/1999 |
| WO | WO-2006/051153 A2 | 5/2006 |
| WO | WO-2007/150030 A2 | 12/2007 |
| WO | WO-2009/064987 A1 | 5/2009 |

OTHER PUBLICATIONS

Luo, C. et al The role of poly(ethylene glycol) in the formation of silver nanoparticles, 2005, JOurnal of Colloid and Interface Science, vol. 288, pp. 444-448.*

(Continued)

*Primary Examiner* — Robert Xu
(74) *Attorney, Agent, or Firm* — Wilmer Cutler Pickering Hale and Dorr LLP

(57) ABSTRACT

The present invention provides nanoparticles having bright fluorescence, where the total number of photons emitted from a single nanoparticle upon excitation with an excitation wavelength of the nanoparticle is at least 107, and giant Raman enhancements, where Raman signal for a molecule near a single nanoparticle increases at least 107 times. The nanoparticles of the invention comprise a plurality of crystallites that are each about 0.6 nm to about 10 nm in size. The present invention also provides methods for making the nanoparticles, which include mixing a matrix material with a reactant capable of being thermally reduced to form the nanoparticle; forming a mixed solid phase; and thermally reducing the mixed solid phase to form the nanoparticle.

42 Claims, 14 Drawing Sheets

(56) References Cited

OTHER PUBLICATIONS

Otsuka, H. et al, PEGylated nanoparicles for biological and pharmaceutical applications, 2003, Advanced Drug Delivery Reviews, vol. 55, pp. 403-419.*

Liu, C. et al. Preparation of silver nanoparticle and its application to the determination of ct-DNA, 2007, Sensor, vol. 7, pp. 708-718.*

Abdullah, et al., "Fluorescent Silver Nanoparticles Via Exploding Wire Technique," Pramana, Journal of Physics, vol. 65, No. 5, Nov. 2005, pp. 815-819.

Baran, et al., "Polarised IR and Raman Spectra of the y-glycine Single Crystal," Spectrochimica Acta Part A, 61, 2005, pp. 1611-1626.

Boyd, et al., "Photoinduced Luminescence from the Noble Metals and its Enhancement on Roughened Surfaces," Physical Review B, vol. 33, No. 12, Jun. 1986, pp. 7923-7936.

Brus, et al., "Electron-electron and Electron-hole Interactions in Small Semiconductor Crystallites: The Size Dependence of the Lowest Excited Electronic State," J. Chem. Phys., 80, May 9, 1984, pp. 4403-4409.

Burstein, et al., ""Giant" Raman Scattering by Adsorbed Molecules on Metal Surfaces," Solid State Communications, vol. 29, pp. 567-570, 1979.

Cao, et al., "Nanoparticles with Raman Spectroscopic Fingerprints for DNA and RNA Detection," Science, vol. 297, Aug. 2002, pp. 1536-1540.

Cavicchioli, et al., "Silver Nanoparticles Synthesized by Thermal Reduction of a Silver(I)-aspartame Complex in Inert Atmosphere," Materials Letters, 59, 2005, pp. 3585-3589.

Chen, et al., "Site-specific Labeling of Proteins with Small Molecules in Live Cells," Current Opinion in Biotechnology, 2005, 16, pp. 35-40.

Dieringer, et al., "Surface Enhanced Raman Spectroscopy: New Materials, Concepts, Characterization Tools, and Applications," Paper, Faraday Discussions, 2006, 132, pp. 9-26.

Du, et al., "Technical and Software Note: PhotochemCAD: A Computer-Aided Design and Research Tool in Photochemistry," Photochemistry and Photobiology, Aug. 1998, vol. 68, No. 2, pp. 141-142.

Emory, et al., "Paper: Re-examining the Origins of Spectral Blinking in Single-Molecule and Single-Nanoparticle SERS," Faraday Discussions, 2006, 132, pp. 249-259.

Fromm, et al., "Exploring the Chemical Enhancemenet for Surface-Enhanced Raman Scattering with Au Bowtie Nanoantennas," The Journal of Chemical Physics, 124, 2006, pp. 061101-1-061101-4.

Fu, et al., "Semiconductor Nanocrystals for Biological Imaging," Current Opinion in Neurobiology, 2005, 15, pp. 568-575.

Gao, et al., "In Vivo Molecular and Cellular Imaging with Quantum Dots," Current Opinion in Biotechnology, 2005, 16, pp. 63-72.

Giepmans, et al., "The Fluorescent Toolbox for Assessing Protein Location and Function," Science, vol. 312, Apr. 2006, pp. 217-224.

International Search Report and Written Opinion of the International Searching Authority, The United States Patent and Trademark Office, for PCT/US2008/083560, dated Apr. 9, 2009, 8 pages.

Jiang, et al, "Feature Article: Single Molecule Raman Spectroscopy at the Junctions of Large Ag Nanocrystals," J. Phys. Chem. B, 2003, 107, pp. 9964-9972.

Jin, et al., "Thermally-Induced Formation of Atomic Au Clusters and Conversion into Nanocubes," J. Am. Chem. Soc., 2004, 126, Mar. 2004, pp. 9900-9901.

Johansson et al., "Surface-enhanced Raman Scattering and Fluorescence Near Metal Nanoparticles," Physics Review B, 2005, vol. 72, pp. 1-18.

Kneipp, et al., "Single Molecule Detection Using Surface-Enhanced Raman Scattering (SERS)," Physical Review Letters, vol. 78, No. 9, Mar. 1997, pp. 1667-1670.

Lin, et al., "Direct Synthesis of Narrowly Dispersed Silver Nanoparticles Using a Single-Source Precursor," Langmuir, 2003, 19, pp. 10081-10085.

Michalet, et al., "Review: Quantum Dots for Live Cells, in Vivo Imaging, and Diagnostics,"Science, vol. 307, Jan. 2005, pp. 538-544.

Moerner, et al., "Review Article: Methods of Single-Molecule Fluorescence Spectroscopy and Microscopy," Review of Scientific Instruments, vol. 74, No. 8, Aug. 2003, pp. 3597-3619.

Nie, et al., "Probing Single Molecules and Single Nanoparticles by Surface-Enhanced Raman Scattering," Science, vol. 275, Feb. 1997, pp. 1102-1106.

Peyser, et al., "Photoactivated Fluorescence from Individual Silver Nanoclusters," Science, vol. 291, Jan. 2001, pp. 103-106.

Peyser-Capadona, et al., "Nanoparticle-Free Single Molecule Anti-Stokes Raman Spectroscopy," Physical Review Letters, 94, Feb. 2005, pp. 058301-1-058301-4.

Rabin, et al., "Light Emission During the Agglomeration of Silver Clusters in Noble Gas Matrices," Journal of Chemical Physics, vol. 108, No. 12, Mar. 1998, pp. 5137-5142.

Saxton, et al., "Single-Particle Tracking: Applications to Membrane Dynamics," Annu. Rev. Biophys. Biomol. Struct., 1997, 26, pp. 373-399.

Shen, et al., "Water-Soluble Fluorescent Ag Nanoclusters Obtained from Multiarm Star Poly(acrylic acid) as "Molecular Hydrogel" Templates," Advanced Materials, 19, 2007, pp. 349-352.

Sonnichsen, et al., "A Molecular Ruler Based on Plasmon Coupling of Single Gold and Silver Nanoparticles," Nature Biotechnology, vol. 23, No. 6, Jun. 2005, pp. 741-745.

Treguer, et al., "Fluorescent Silver Oligomeric Clustes and Colloidal Particles," Solid State Sciences, 7, 2005, pp. 812-818.

Tsien, R., "Opinion: Imagining Imaging's Future," Perspective, Nature, Sep. 2003, pp. SS16-SS21.

Wang, et al., "The Structural Basis for Giant Enhancement Enabling Single-Molecule Raman Scattering," PNAS, Jul. 2003, vol. 100, No. 15, pp. 8638-8643.

Wertheim, et al., "Cluster Growth and Core-Electron Binding Energies in Supported Metal Clusters," Physical Review B., vol. 37, No. 2, Jan. 1988, pp. 844-847.

Zhao, et al., "Pyridine-$Ag_{20}$ Cluster: A Model System for Studying Surface-Enhanced Raman Scattering," J. Am. Chem. Soc., 2006, 128, pp. 2911-2919.

Zheng, et al., "Luminescent and Raman Active Silver Nanoparticles with Polycrystalline Structure," J. Am. Chem. Soc., 2008, 130, pp. 10472-10473.

* cited by examiner

GRANULAR NANOPARTICLES HAVING BRIGHT FLUORESCENCE AND GIANT RAMAN ENHANCEMENTS

CROSS-REFERENCE TO RELATED APPLICATION

This application is the national phase application of International Patent Application No. PCT/US2008/083560, filed on Nov. 14, 2008, which claims the benefit of the filing date of U.S. Patent Application No. 60/988,283, filed on Nov. 15, 2007, the content of which are hereby incorporated by reference herein in their entirety.

STATEMENT REGARDING FEDERALLY SPONSORED RESEARCH OR DEVELOPMENT

This invention was made with government support under 0646094 and 0238773 awarded by the National Science Foundation. The government has certain rights in the invention.

COPYRIGHT NOTICE

This patent disclosure may contain material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present invention relates to nanoparticles and methods for making the same. More particularly, the present invention relates to nanoparticles having bright fluorescence and giant Raman enhancements and methods for making the same.

BACKGROUND OF THE INVENTION

Fluorescent probes, such as organic dyes, fluorescence proteins and quantum dots, have enabled many discoveries in modern biology by allowing molecular and cellular processes to be imaged with high spatial and temporal resolutions. Noble metals also exhibit versatile optical properties at the nanometer scales, providing exciting opportunities for the development of imaging probes and sensors.

Raman enhancement has been observed in noble metal nanostructures deposited onto substrates, but the presence of a substrate limit their potential applications to a wider range of uses, such as imaging of molecules, metabolites, and drugs in cells. Raman enhancements have also been observed from encapsulated few-atom silver clusters, but the low synthesis yield of these clusters makes their potential application to bioimaging difficult to realize.

Moreover, metal nanoparticles with diameters above the Fermi wavelength (~1 nm) normally do not luminesce, although a very small fraction (≤3%) of the nanoparticles has been observed to exhibit fluorescence and Raman enhancements. However, it is unclear why certain nanoparticles exhibit fluorescence and Raman enhancements while majority of the other nanoparticles do not. Moreover, it is difficult to isolate this small fraction because the structural mechanisms responsible for the fluorescence and Raman activities are not well understood.

SUMMARY OF THE INVENTION

Nanoparticles that exhibit bright fluorescence and/or giant Raman enhancements are described. Methods for synthesizing nanoparticles that exhibit bright fluorescence and/or giant Raman enhancements are also described.

In accordance with certain embodiments, a nanoparticle having a plurality of crystallites within the nanoparticle is described, where the crystallites are each about 0.3 nm to about 10 nm in size, and the total number of photons emitted from the nanoparticle upon excitation with an excitation wavelength of the nanoparticle is at least $10^{11}$.

In accordance with certain embodiments, a composition having a plurality of nanoparticles, each nanoparticle having a plurality of crystallites that are about 0.3 nm to about 10 nm in diameter is described. In certain embodiments, at least 5% of the plurality of nanoparticles exhibit fluorescence where the total number of photons emitted from each nanoparticle upon excitation with an excitation wavelength of the nanoparticle is at least $10^7$.

In accordance with certain embodiments, a method for producing a nanoparticle having a plurality of crystallites within the nanoparticle is described, where the crystallites are each about 0.6 nm to about 10 nm in size, and the total number of photons emitted from the nanoparticle upon excitation with an excitation wavelength of the nanoparticle is at least $10^7$.

In accordance with certain embodiments, the method includes mixing a matrix material with a reactant capable of being thermally reduced to form the nanoparticle, wherein the matrix material has a melting temperature of at least 100° C.; forming a mixed solid phase comprising the matrix material and the reactant; and thermally reducing the mixed solid phase to form the nanoparticle.

BRIEF DESCRIPTION OF THE DRAWINGS

The above and other objects and advantages of the present invention will be apparent upon consideration of the following detailed description, taken in conjunction with the accompanying drawings, and in which.

DETAILED DESCRIPTION OF THE INVENTION

Figure 1A:
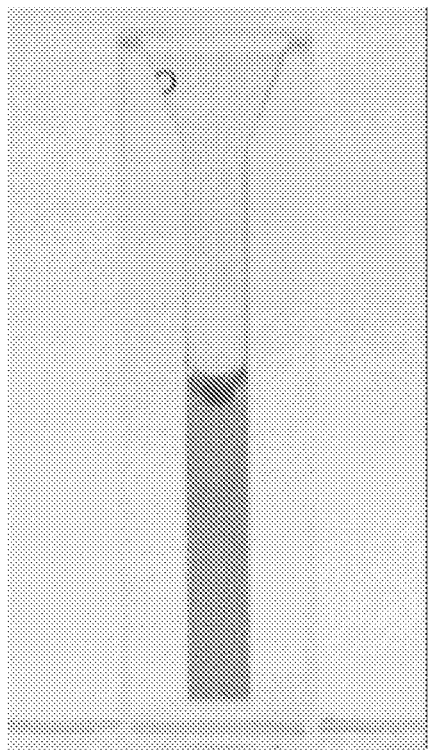
FIG. 1A is a photograph of a nanoparticle solution produced in accordance with certain embodiments of the present invention.

Nanoparticles having bright fluorescence and giant Raman enhancements and methods for making the same are described. The nanoparticles can serve as fluorescent probes and sensitive reporters of any type of molecules, such as small molecules, and for use in chemical imaging of biological materials, such as live cells.

As used herein, "bright fluorescence" is meant to denote fluorescence from individual nanoparticles where the total number of photons emitted (i.e., a lifetime average of emitted photons) is at least $10^7$, for example at least $10^8$, $10^9$, $10^{10}$, or $10^{11}$. As would be apparent to one of ordinary skill in the art, the total number of emitted photons may be approximately the point at which photobleaching can occur, where additional photons are not emitted even with further excitation. For example, while the while total number of emitted photons from nanoparticles irradiated with a high powered laser may be reached at an earlier time than those nanoparticles irradiated with a low powered laser, the total number of photons emitted are substantially the same. In certain embodiments, the total number of photons emitted from individual bright fluorescent nanoparticles can exceed the total number of photons emitted from single quantum dots or dye molecules by at least 2 orders of magnitude. In particular, the total number photons emitted from individual nanoparticles can exceed the total number of photons emitted from dye molecules by at least 5 orders of magnitude.

As used herein, "giant Raman enhancements" is meant to denote Raman signal enhancement of at least $10^7$, for example at least $10^8$, $10^9$, $10^{10}$, $10^{11}$, $10^{12}$, $10^{13}$, $10^{14}$, or $10^{15}$, for one or more molecules near a nanoparticle of the present invention. As would be readily apparent to one of ordinary skill in the art, Raman enhancement represents the degree of signal amplification that can be achieved during detection of a particular material. For example, giant Raman enhancements may allow a vibrational spectrum, or the chemical fingerprint, of a single molecule, such as a single small molecule, to be obtained when near a nanoparticle exhibiting giant Raman enhancement whereas the vibrational spectrum of the single molecule may be too weak for detection in the absence of the nanoparticle.

Nanoparticles

Nanoparticles exhibiting bright fluorescence and/or giant Raman enhancement can be polycrystalline. For example, the nanoparticles can contain crystallites that are about 0.3 nm to about 10 nm in size. In certain embodiments, the size of the crystallites can range from about 1 nm to about 3 nm in size. The size of the crystallites may vary or may be uniform within the individual nanoparticles.

The nanoparticles can contain grain boundaries that delineate neighboring crystallites. A grain boundary is the interface between two grains in a polycrystalline material. For example, individual nanoparticles can contain about 2 to 10,000 grain boundaries. In certain embodiments, the number of grain boundaries can range from about 100 to about 2,000.

Without wishing to be bound by theory, it may be possible that the crystallites present in the nanoparticles can result in discrete energy states that give rise to fluorescent optical transitions. Accordingly, the bright fluorescence exhibited by the nanoparticles is not limited to any particular diameter of the nanoparticles.

However, suitable nanoparticles can range from about 1 nm to about 1000 nm in diameter. In certain embodiments, the diameter of the nanoparticles can range from about 1 nm to about 500 nm. In some embodiments, the diameter of the nanoparticles can range from about 1 nm to about 20 nm. In some other embodiments, the diameter of the nanoparticles can range from about 3 nm to about 18 nm.

The nanoparticles can be made of at least one metal, such as a noble metal and/or a transition metal. Some suitable exemplary metals include gold, silver, tantalum, platinum, palladium, rhodium, copper, and mixtures thereof.

In certain embodiments, a collection, dispersion, and/or solution of nanoparticles is described, where at least 5%, 15%, 30%, 50%, 75%, 90%, 95%, or 97% of the nanoparticles in the collection, dispersion, and/or solution exhibit bright fluorescence and/or giant Raman enhancements. Moreover, a collection, dispersion, and/or solution of non-aggregated nanoparticles can include individual nanoparticles that exhibit bright fluorescence and/or giant Raman enhancements. In certain embodiments, at least 5%, 15%, 30%, 50%, 75%, 90%, 95%, or 97% of the non-aggregated individual nanoparticles in the collection, dispersion, and/or solution exhibit bright fluorescence and/or giant Raman enhancements.

Synthesis

According to certain embodiments, nanoparticles can be prepared by carrying out a solid phase thermal reduction reaction. A reactant that can be reduced to the desired nanoparticle having bright fluorescence and giant Raman enhancement can be mixed with a matrix material to undergo a solid phase thermal reduction reaction. For example, noble metal nanoparticles can be synthesized by mixing a noble metal ion salt ("reactant") with an organic material that functions as the matrix during the solid phase thermal reduction reaction.

Without wishing to be bound by theory, the solid phase thermal reduction reaction may be beneficial because the solid matrix phase may be able to control the nucleation, migration, and rearrangement of reduced atoms of the nanoparticles.

In certain embodiments, the matrix material may be utilized in stoichiometric excess compared to the reactant, wherein the number of moles of the matrix material utilized is higher than the number of moles of the reactant utilized. For example, suitable stoichiometric ratios of matrix material: reactant can range from about 2:1 to about 50:1. In certain embodiments, stoichiometric ratios of matrix material: reactant can range from about 5:1 to about 30:1. Particularly, stoichiometric ratios of matrix material: reactant can range from about 15:1 to about 25:1.

Some examples of a reactant that can be reduced to the desired nanoparticle having bright fluorescence and giant Raman enhancement include metal ion salts, such as acetates, chlorates, cyanides, formates, halides, iodides, nitrates, perchlorates, phosphates, sulfates, and/or sulfides of metals, such as noble or transition metals. Some exemplary suitable metals include copper, gold, silver, tantalum, platinum, palladium, and/or rhodium.

In certain embodiments, matrix material that can be utilized include materials that remain as a solid at temperatures sufficient to carry out thermal reduction of the reactant. For example, the matrix material has a melting point of at least 100° C., such as at least 120° C., 140° C., 150° C., 160° C., 180° C., 200° C., 220° C., and the like. The matrix material can be an organic material, an inorganic material, and/or salts thereof. Moreover, suitable matrix materials include materials that can be preferentially dissolved after formation of the nanoparticles to enable separation of the nanoparticles from the matrix material.

Some examples of suitable organic matrix materials that can be included in the solid phase reaction include amino acids, such as alanine, arginine, asparagine, aspartic acid, cysteine, glutamic acid, glutamine, glycine, methionine, phenylalanine, proline, serine, threonine, tryptophan, tyrosine, and valine. Other examples of suitable organic materials include dipeptides, such as aspartame, carnosine, anserine, homoanserine, kyotorphin, balenine, glorin, barretin, and pseudoproline. Some other examples of suitable organic materials include tripeptides, such as glutathione, melanostatin, ophthalmic acid, norophthalmic acid, eisenin, and the like. Some other examples of suitable organic materials include oligomers or polymers, such as polyethylene glycol, polyethylene, polysiloxane, and the like.

Some other exemplary inorganic matrix materials include sodium acetate, sodium phosphate, sodium hexametaphosphate, sodium fluorophosphate, sodium phosphate dibasic dodecahydrate, potassium acetate, potassium trifluoroacetate, sodium ammonium phosphate tetrahydrate, magnesium phosphate hydrate, calcium acetate hydrate, and/or salts thereof.

In certain embodiments, the matrix material can be attached to the nanoparticles through covalent, ionic, or van der Waals interactions. For example, the matrix material may contain functional groups, such as SH, COOH, NH, and the like, that allows the matrix material to bind to the nanoparticles.

In some other embodiments, the matrix material can be a bifunctional material containing additional functional groups, such as SH, COOH, NH, OH, and the like. One of the functional group may interact with the nanoparticles through covalent, ionic, or van der Waals interactions and the other functional group may further react other complementary chemical moieties after or before the matrix material is bound to the nanoparticles. In some other embodiments, the matrix material can contain more than two functional groups, such as three, four, five, or six different functional groups.

In certain embodiments, the reactant and the matrix material are mixed, either in solid phase or using a solvent. After mixing, any solvent that may be present can be removed by, for example, evaporation, vacuum, and the like to form a mixed solid phase. After forming the mixed solid phase, the temperature can be increased to a temperature sufficient for thermal reduction to occur and to cause the formation of the nanoparticles. Some suitable thermal reduction reaction temperatures include 100-300° C., 150-250° C., 180-220° C., 190-210° C., and the like. Some suitable thermal reduction reaction pressures include 0.5-1.5 atm, 0.7-1.3 atm, 0.9-1.1 atm, and the like.

After the thermal reduction, any number of post processing operations can be carried out. For example, the organic material (or, in certain embodiments, any excess not bound to the nanoparticles) can be dissolved using a suitable solvent, such as water, to release the nanoparticles. Sonication, stirring, and the like can be utilized to assist dissolution of the organic material. The nanoparticles may also be dispersed throughout the solvent.

Upon dissolution of the organic material, separation of the nanoparticles from the liquid phase can be carried out using, for example, centrifugation. Some other exemplary separation technique includes gel separation, such as electrophoresis where separation based on mass/charge of nanoparticles can be achieved.

Upon collection of the nanoparticles, further separation, sorting, or characterization of the nanoparticles can be carried out, such as to separate the nanoparticles based on desired sizes using, for example, centrifugation, filtration, and the like.

Applications

Nanoparticles having bright fluorescence and/or giant Raman enhancement can be utilized in a number of different applications. For example, the nanoparticles can be utilized as sensors, as photosensitizers, as building blocks to create other hybrid nanomaterials, as biocarriers, and the like. Moreover, some nanoparticles are biocompatible. In that instance, due to their biocompatibility, bright fluorescence, and/or giant Raman enhancements, nanoparticles of the present invention are useful as biolabels, robust fluorescent probes and sensitive reporters of small molecules in biological applications.

Sensors

Nanoparticle described herein can be utilized as a variety of different sensors. For example, nanoparticles described herein can be tethered on a substrate to detect small molecules such as $CO$, $CH_3CN$, $NH_3$, and the like. The nanoparticles can be tethered onto a substrate by, for example, using a bifunctional molecule where one end of the molecule binds to the surface of a substrate and the other end of the molecule binds to the nanoparticle.

In certain embodiments, the nanoparticles described herein can be biocompatible and serve as useful biosensors. For example, nanoparticle described herein can be utilized to study the biochemical interaction between two objects, such as a molecule, cell, tissues, organ, and the like, under in vivo or in vitro conditions. As one non-limiting example, nanoparticles having bright fluorescence and giant Raman enhancements can be integrated with viral protein capsid to probe the biochemical interactions involved in viral endocytosis. Endocytosis is a process whereby molecules such as proteins are engulfed by the cell membrane and become absorbed into the cell. Combined with tracking and spectroscopy techniques, nanoparticles described herein can reveal heterogeneity in the biochemical interactions during viral endocytosis at the single particle level.

In some other embodiments, the nanoparticles described herein can be utilized as gene delivery vectors that also serve as biosensors. Certain biocompatible metal nanoparticles can enter live cells to be used as delivery vectors for gene therapy. Bright fluorescence and giant Raman enhancement characteristic can further help to elucidate the delivery mechanism at the single particle level.

Solar Cells

Nanoparticles described herein can also be utilized as photosensitizers to convert light energy into electricity. As described above, nanoparticles described herein have absorption cross sections that are at least 100 times larger than the conventional organic dyes. Accordingly, nanoparticles described herein can more effectively absorb and harvest photons as compared to organic dyes and semiconductor materials.

Building Blocks for Hybrid Nanomaterials

Nanoparticles described herein can also be utilized as building blocks to form other hybrid nanomaterials. For example, nanoparticles which fluoresce under different excitation wavelengths can be coupled together with complementary organic coatings to form a dimer-like structure that fluoresce under two different excitation wavelengths.

Nanoparticles described herein can also be used as building blocks to create other hybrid nanomaterials and find applications in energy conversion, information technology and in vivo imaging.

EXAMPLE

Silver Nanoparticles

Silver nanoparticles were prepared as follows. Glycine (150 mg, 1.998 mmol) and silver nitrate (15 mg, 0.0883 mmol) were dissolved in distilled water. The water was evaporated to obtain a mixed solid phase. The mixed solid phase was heated to 445 K (172° C.) to allow thermal reduction of the reactant to take place. The completion of the thermal reduction was monitored by observing a color change from white to brown. However, more quantitatively techniques, such as differential scanning calorimeter, can be utilized as well.

To purify the nanoparticles, the reaction product was suspended in 10 ml distilled water and sonicated for 24 hours. The insoluble aggregates were removed using centrifugation at 6000 g for 10 min. To remove free glycine molecules and ions, the solution was then centrifuged at 16000 g for 15 min and the pellet containing the nanoparticles was collected and re-suspended in water. This process was repeated at least four times.

Figure 1B:
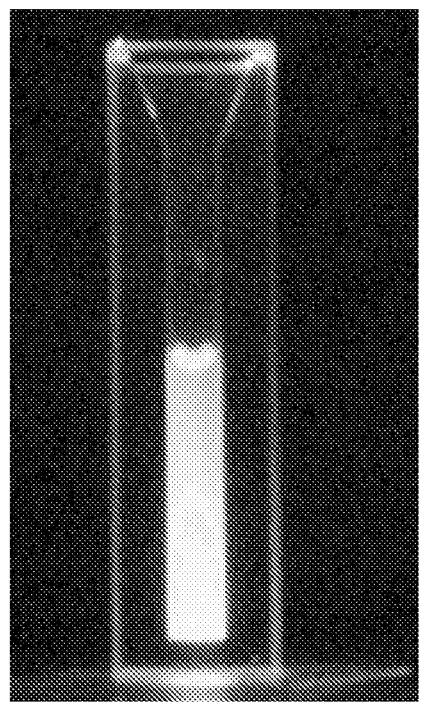
FIG. 1B is a photograph of the nanoparticle solution of FIG. 1A exhibiting fluorescence in accordance with certain embodiments of the present invention.

The final solution contained silver nanoparticles with diameters ranging from 2 to 30 nm. As shown in FIGS. 1A and 1B, the nanoparticles fluoresce strongly with a 532 nm laser excitation. FIG. 1A shows the nanoparticle solution without any laser excitation, and FIG. 1B shows the fluorescing nanoparticle solution with 532 nm laser excitation, where a 545 nm long-pass filter was used to block the scattered laser light. The nanoparticles remained stable in solution for many months at ambient conditions.

Transmission electron microscopy was utilized to carry out the structural characterization of the nanoparticles after size-selective separation. Low-resolution TEM images were obtained using a 200 keV JEOL 2010 TEM. High-resolution TEM images were obtained using a 400 keV JEM-4000EX TEM.

Figure 2A:
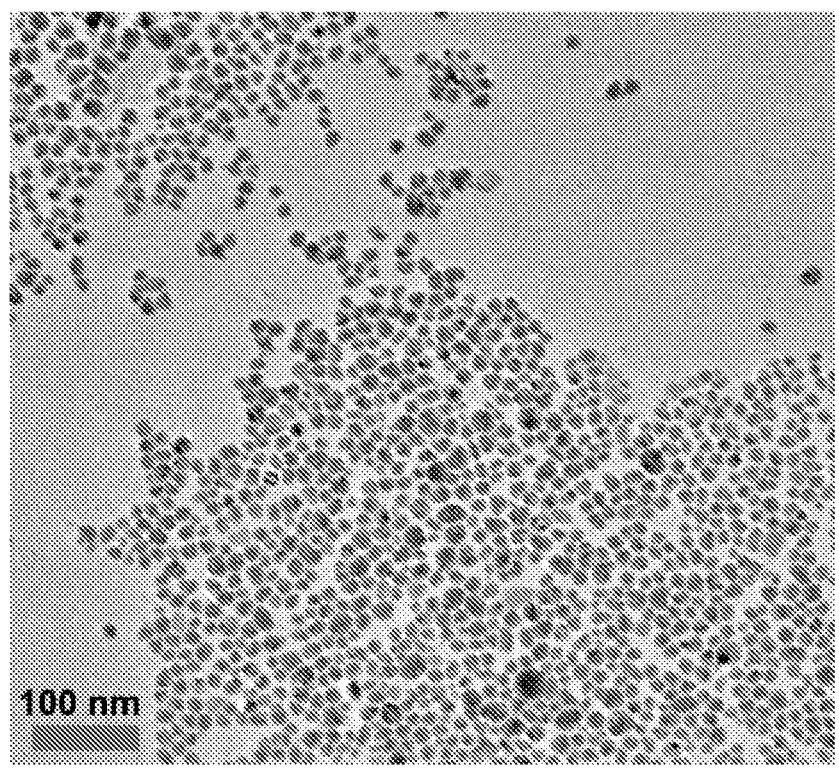
FIG. 2A is a low resolution transmission electron microscope (TEM) image of silver nanoparticles with average diameter of 18 nm produced in accordance with certain embodiments of the invention.
Figure 2B:
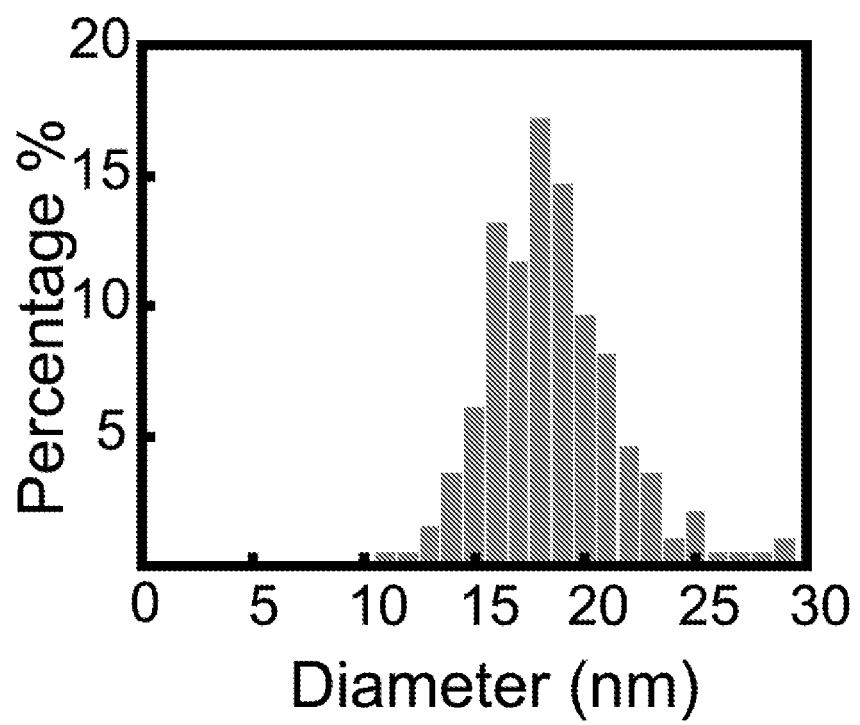
FIG. 2B is a graph showing the distribution of nanoparticles' diameters as determined from the TEM image of FIG. 2A in accordance with certain embodiments of the invention.
Figure 2C:
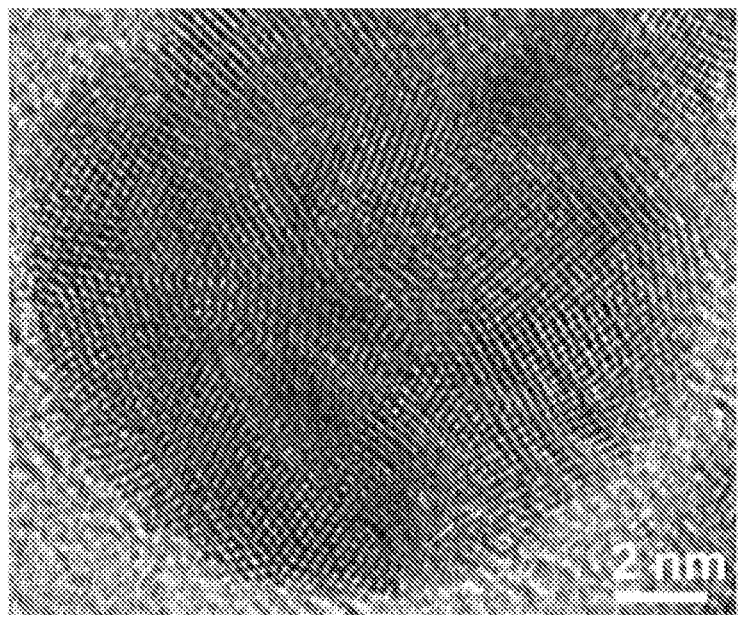
FIG. 2C is a high resolution TEM image of a silver nanoparticle shown in FIG. 2A having a high number of crystallites within the nanoparticle in accordance with certain embodiments of the invention.

After centrifugation at 8000 g, nanoparticles with diameters of 18±3 nm were obtained from the pellet (FIGS. 2A, B, and C). FIG. 2A shows a low-resolution TEM image; FIG. 2B shows a graph illustrating the relative number of nanoparticles with certain diameters obtained from low resolution TEM images, e.g., a particle diameter distribution, and FIG. 2C shows a magnified view of a single nanoparticle.

Figure 3A:
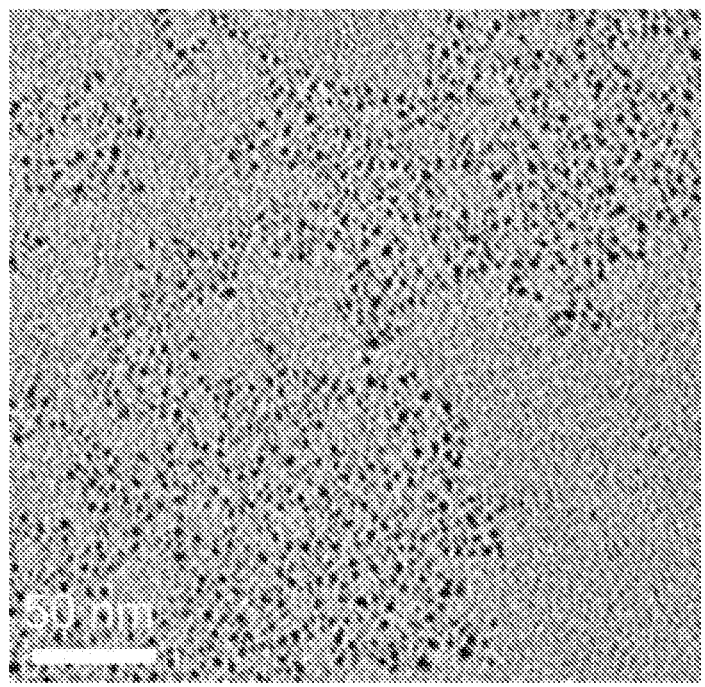
FIG. 3A is a low resolution transmission electron microscope (TEM) image of silver nanoparticles with average diameter of about 2-3 nm produced in accordance with certain embodiments of the invention.
Figure 3B:
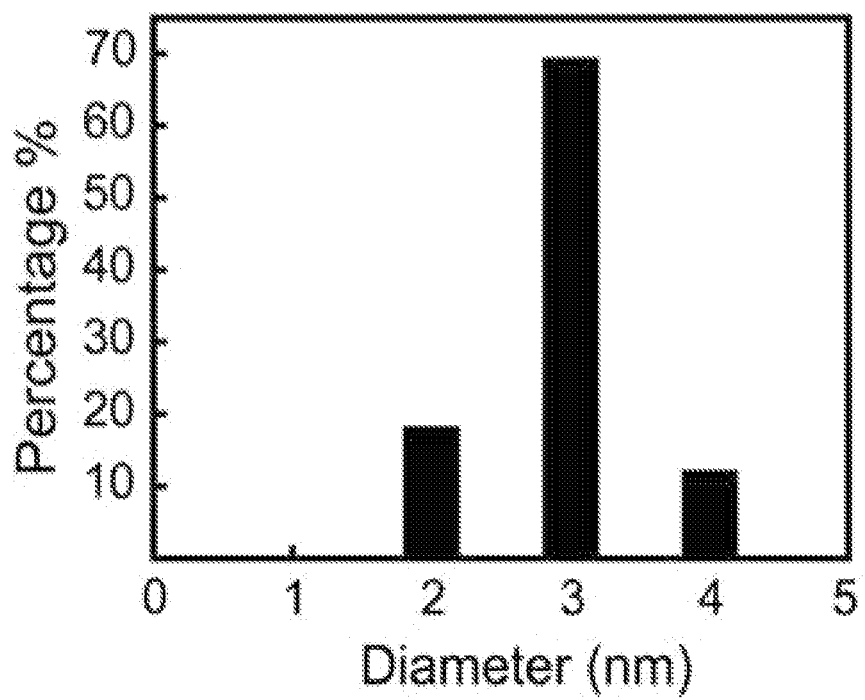
FIG. 3B is a graph showing the distribution of nanoparticles' diameters as determined from the TEM image of FIG. 3A in accordance with certain embodiments of the invention.
Figure 3C:
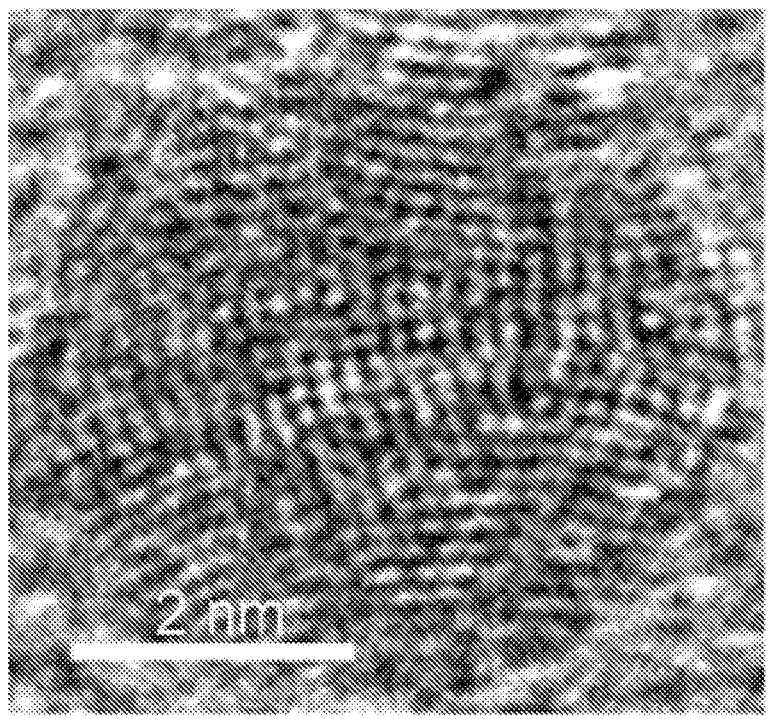
FIG. 3C is a high resolution TEM image of a silver nanoparticle shown in FIG. 3A having a high number of crystallites within the nanoparticle in accordance with certain embodiments of the invention.

After centrifugation at 15000 g, nanoparticles with diameters of 3±1 nm were obtained from the supernatant and the larger particles in the pellet were removed to provide particles of extremely small and uniform diameters (FIGS. 3A, B, and C). FIG. 3A shows a low-resolution TEM image of the size-selected nanoparticle, FIG. 3B shows a graph illustrating the relative number of nanoparticles with certain diameters obtained from low resolution TEM images, and FIG. 3C shows a magnified view of a nanoparticle.

Except as otherwise noted, the remainder of this example reports the properties of the 18 nm nanoparticles.

Figure 4A:
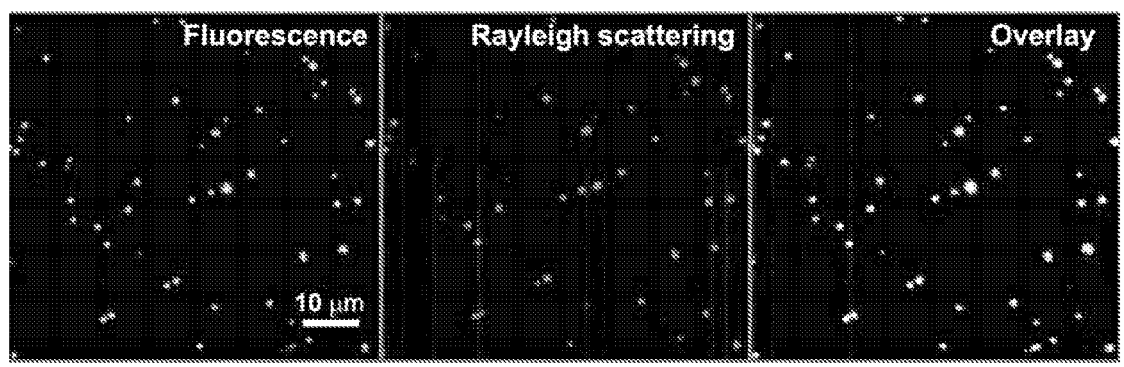
FIG. 4A are fluorescence, Rayleigh scattering, and overlay images of the silver nanoparticles produced in accordance with certain embodiments of the invention.
Figure 4B:
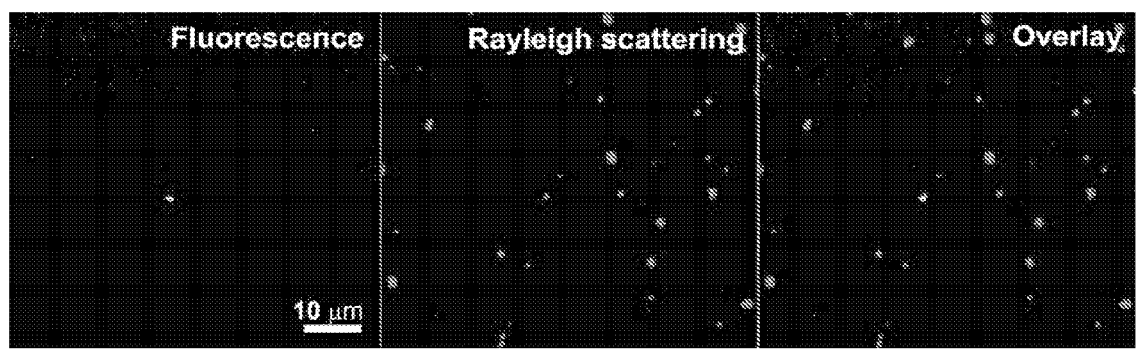
FIG. 4B are fluorescence, Rayleigh scattering, and overlay images of commercially available 20 nm silver nanoparticles produced by solution-phase synthesis.

The fluorescence emission of the 18 nm silver nanoparticles dispersed in water was detected. As shown in FIG. 4A, comparison of the Rayleigh scattering (dark field) and fluorescence images revealed that more than 95% of the nanoparticles were fluorescent. This was in contrast to colloidal silver nanoparticles prepared by conventional solution phase synthetic methods, which shows that only a few of the nanoparticles identified by Rayleigh scattering were fluorescent (see FIG. 4B).

Figure 5A:
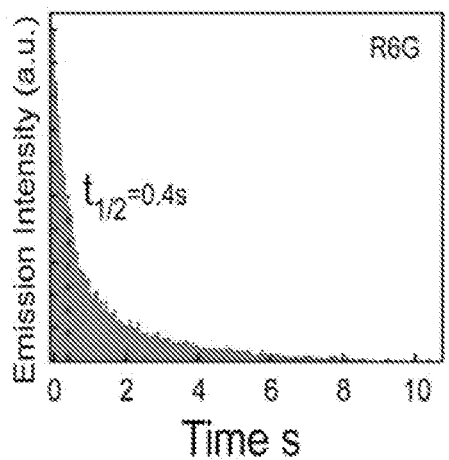
FIG. 5A is an emission spectrum from Rhodamine 6G, showing a half lifetime for photobleaching of about 0.4 seconds.
Figure 5B:
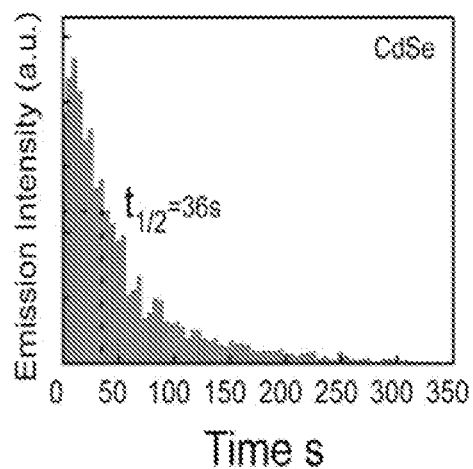
FIG. 5B is an emission spectrum from CdSe/ZnS core-shell quantum dots, showing a half lifetime for photobleaching of about 36 seconds.
Figure 5C:
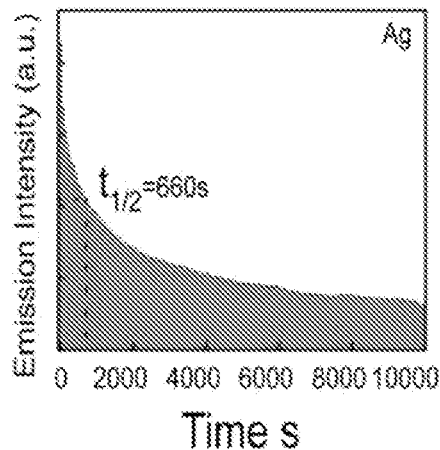
FIG. 5C is an emission spectrum from the fluorescent silver nanoparticles of the present invention, showing a half lifetime for photobleaching of about 660 seconds.

Emission from the silver nanoparticles prepared in accordance with certain embodiments of the invention was bright and photostable: under the excitation conditions where half lifetime of Rhodamine 6G (R6G) photobleaching is about 0.4 s (see FIG. 5A), the half lifetimes of quantum dots and silver nanoparticles are about 36 s (see FIG. 5B) and 660 s (see FIG. 5C).

The individual silver nanoparticles on average emitted a total of about $7 \times 10^{10}$ photons before photobleaching. This number was about 2 orders of magnitude larger than the total number of photons emitted by single quantum dots ($\sim 9 \times 10^8$, CdSe/ZnS core-shell quantum dots, emission maximum 605 nm, purchased from Invitrogen, Inc.) and 5 orders of magnitude larger than the total number of photons emitted by single organic dye molecules ($\sim 10^6$, Rhodamine 6G) before photobleaching.

Figure 6:
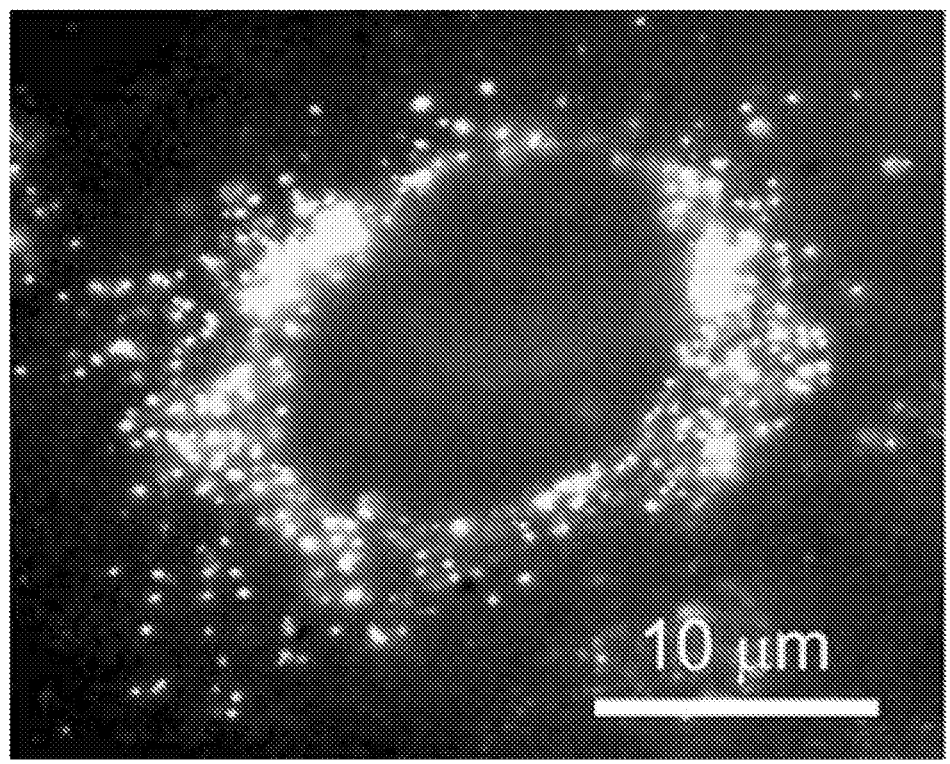
FIG. 6 is a fluorescence microscope image of a HeLa cell stained with the fluorescent silver nanoparticles of the present invention.

The silver nanoparticles were also compatible with cell imaging—fluorescence from the particles attached to a live cell was not quenched but showed similar intensity as measured as a dispersion in water. The nanoparticles were incubated with live HeLa cells (purchased from ATCC) at 37° C. After 10 minutes, the cells were washed using Minimum Essential Medium (purchased from INVITROGEN) and imaged directly on the fluorescence microscope with epigeometry. Some of the nanoparticles entered cells, likely by endocytosis, and exhibited directed microtubule-dependent movement. Others were stationary and likely remained on the cell surface (see FIG. 6).

A high-resolution TEM was utilized to probe structural differences between the fluorescent silver nanoparticles created by methods in accordance with the present invention and the commercially available non-fluorescent silver particles of similar sizes (~20 nm in diameter) produced by solution phase synthesis, which were purchased from Ted Pella, Inc.

Figure 7A:
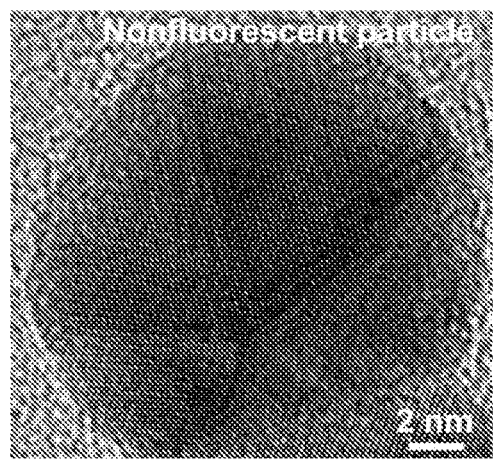
FIG. 7A is a high resolution TEM image of a commercially available 20 nm silver nanoparticles produced by solution-phase synthesis showing a low number of crystallites within the nanoparticle.
Figure 7B:
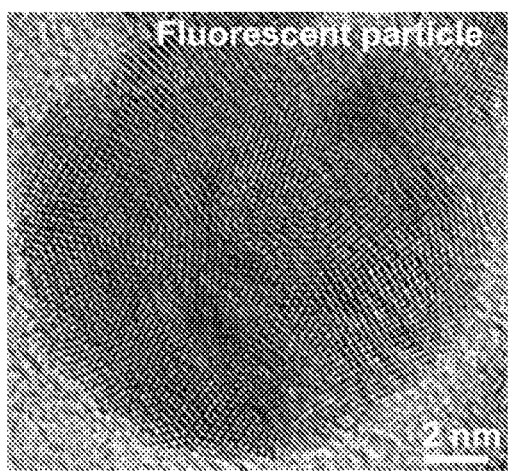
FIG. 7B is a high resolution TEM image of a silver nanoparticle produced in accordance with certain embodiments of the invention showing a high number of crystallites within the nanoparticle.
Figure 7C:
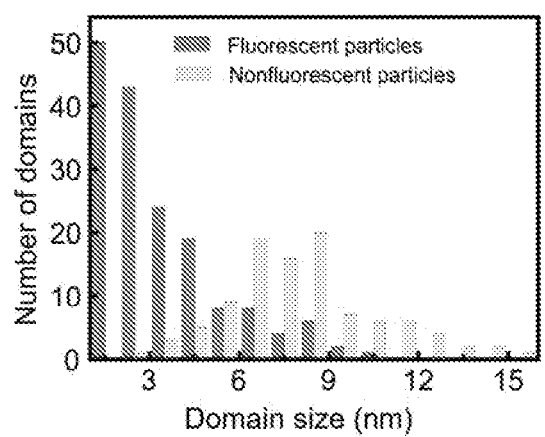
FIG. 7C is a graph showing the crystallite size distribution within the nanoparticles for 15 of these nanoparticles shown in FIG. 7A and FIG. 7B.

As shown in FIGS. 7A through 7C, even though the non-fluorescent particles were of comparable particle diameters, the non-fluorescent nanoparticles generally showed single-crystalline or large twin structures with average crystallite size of about 8 nm (see FIGS. 7A and 7C). In contrast, fluorescent nanoparticles displayed a highly granular structure with many small crystallite and grain sizes of about the 1-2 nm range (see FIGS. 7B and 7C). Crystallites that are smaller than 1 nm may also be present but not resolved by TEM.

Figure 8:
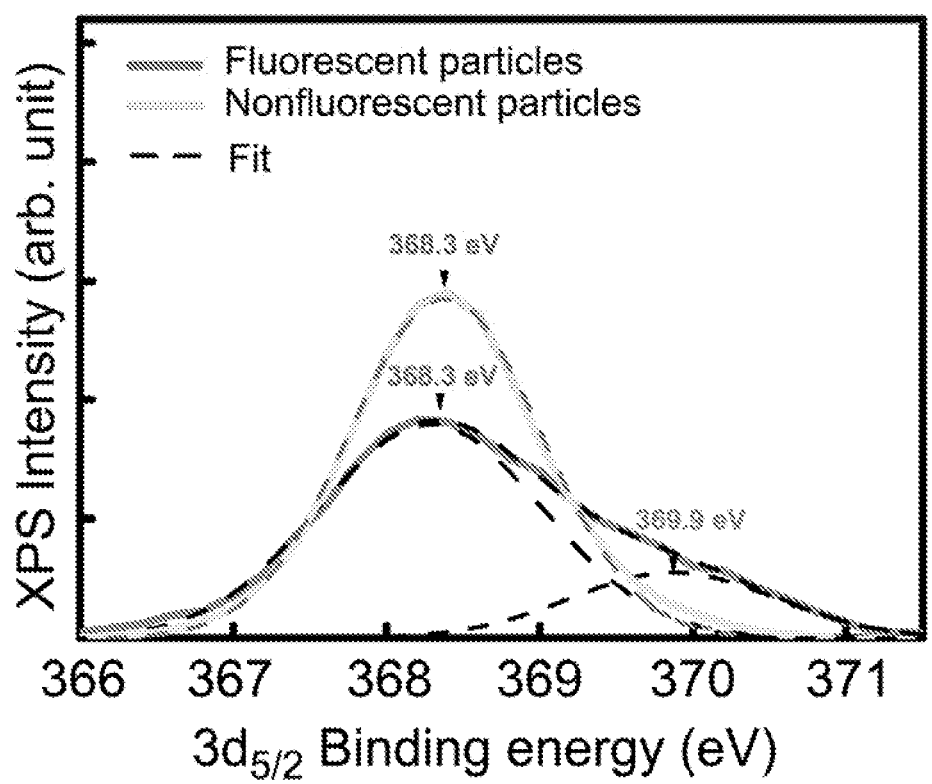
FIG. 8 are x-ray photoelectron spectra (XPS) of the fluorescent nanoparticles of the present invention (labeled "Fluorescent particles") and non-fluorescent, commercially available silver nanoparticles (labeled "Nonfluorescent particles"), where Gaussian curve fit (labeled "Fit") for the non-fluorescent nanoparticles is centered at 368.3 eV and two Gaussian curve fits (labeled "Fit") for the fluorescent nanoparticles are centered at 369.9 eV and 368.3 eV.

Furthermore, because the binding energy (BE) of the nanoparticle shifts from the bulk metal value, with the shift inversely proportional to the particle size, we measured the BE spectrum of the fluorescent and non-fluorescent nanoparticles using X-ray photoelectron spectroscopy. As shown in FIG. 8, the BE spectrum of the non-fluorescent nanoparticles (light solid line, labeled as "Nonfluorescent particles") showed a single peak at 368.3 eV, agreeing quantitatively with the bulk value previously determined for silver (368.1 eV). In contrast, the spectrum of the fluorescent nanoparticles (dark solid line, labeled as "Fluorescent particles") was asymmetric with substantial additional contributions at higher BE. Fitting the spectrum with multiple Gaussians yielded two major peaks at 368.3 eV and 369.9 eV (dashed lines, labeled as "Fit"). The extra peak at 369.9 eV indicates an 1.8 eV shift from the bulk silver value, corresponding to an average grain size of 0.9 nm.

Without wishing to be bound by theory, it may be possible that the small domains present in the nanoparticles result in discrete energy states that give rise to fluorescent optical transitions. If true, this suggest that smaller nanoparticles with a similar granular structure may also exhibit bright fluorescence.

Figure 9:
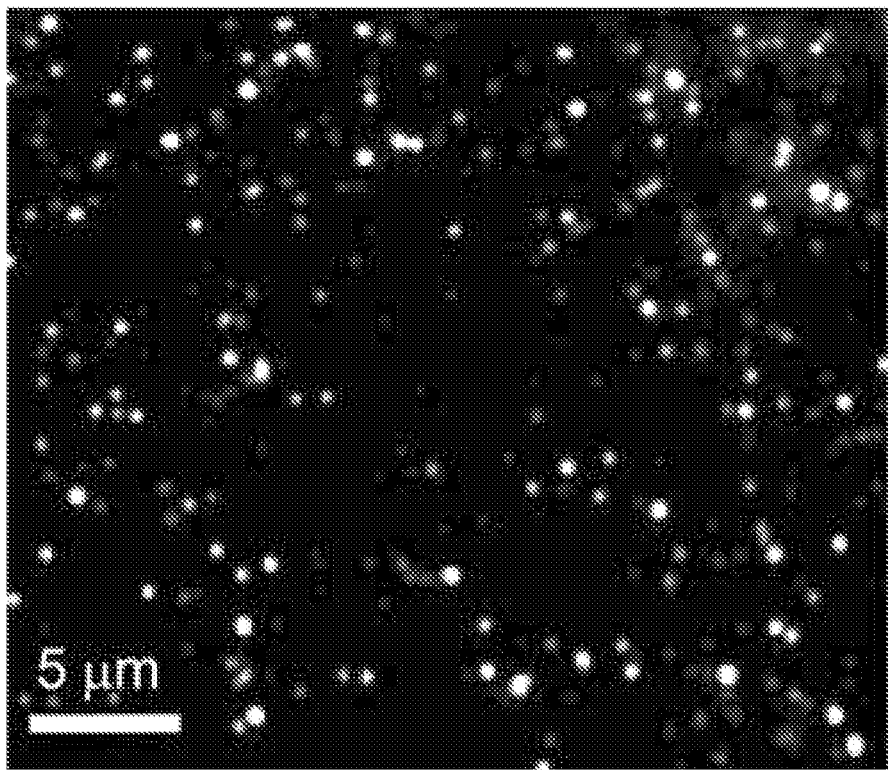
FIG. 9 is a fluorescence image of silver nanoparticles with average diameter of about 2-3 nm produced in accordance with certain embodiments of the present invention.

As shown in FIG. 3C, the 3 nm nanoparticles also exhibited similar granular structure within the nanoparticles, with crystallite sizes of about 1 nm or less. Indeed, as shown in FIG. 9, the 3 nm nanoparticles were highly fluorescent as well, emitting on average $4 \times 10^9$ photons before photobleaching.

Figure 10A:
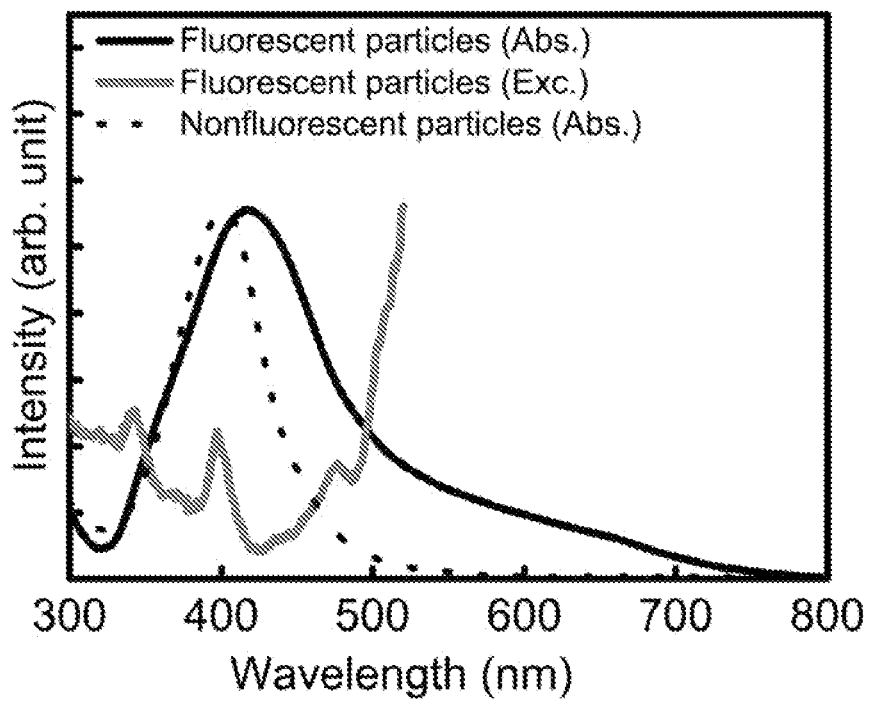
FIG. 10A shows an absorption spectrum of 20 nm non-fluorescent, commercially available nanoparticle (labeled "Nonfluorescent particles (Abs).") and absorption and excitation spectra of 18 nm fluorescent silver nanoparticles in accordance with certain embodiments of the present invention (labeled "Fluorescent particles (Abs.)" and "Fluorescent particles (Exc.)," respectively), wherein the excitation spectrum exhibits peaks at 342 nm, 398 nm, and 476 nm.

In addition, the absorption, excitation and emission spectra of the 18 nm nanoparticles were measured. As shown in FIG. 10A, the absorption spectrum (dark solid line, labeled as "Fluorescent particles (Abs.)") displayed a peak near the plasmon resonance of non-fluorescent silver nanoparticles, but with a significantly broader width, suggesting the presence of additional optical transitions in the fluorescent particles.

However, as shown in FIG. 10A, the fluorescence excitation spectrum (light solid line, labeled as "Fluorescent particles (Exc.)") adopted an almost opposite trend, exhibiting a minimum at the absorption peak.

Without wishing to be bound by theory, this surprising observation may indicate that the fluorescence did not arise from the collective excitation modes of free electrons (plasmons) that dominate the absorption of silver. Instead, the fluorescence may have resulted from single-electron excitations due to the small silver domains of the nanoparticles.

Figure 10B:
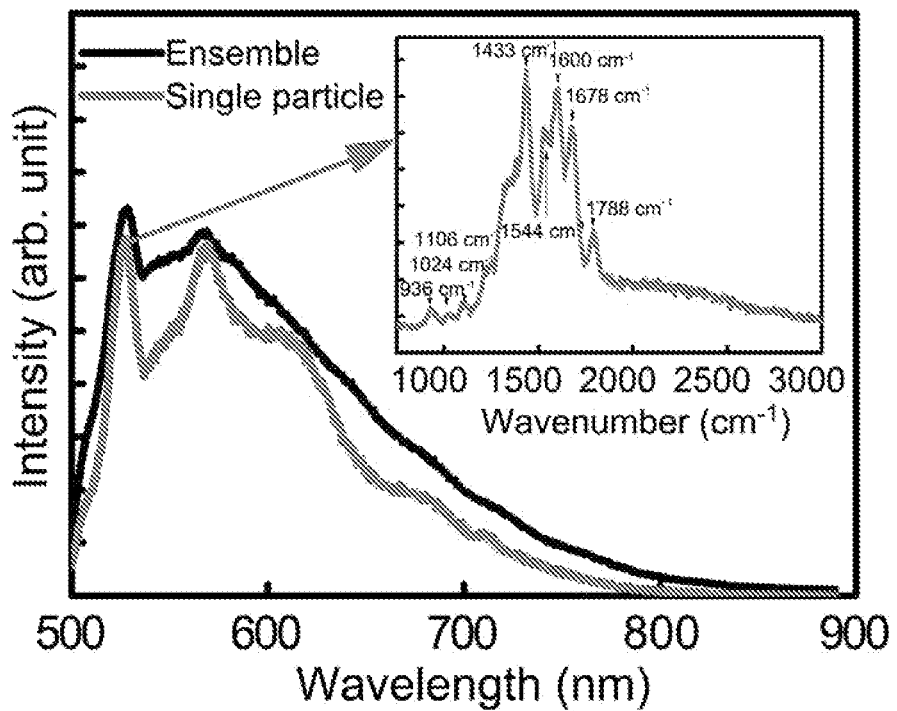
FIG. 10B shows emission spectra of a single fluorescent nanoparticle (labeled "Single particle") and an ensemble of fluorescent nanoparticles (labeled "Ensemble") in accordance with certain embodiments of the present invention, wherein the inset shows further resolved Raman peak of the single nanoparticle emission spectrum obtained by using a high-density grating, showing multiple lines that correspond to various vibrational modes of glycines in accordance with certain embodiments of the present invention.

Consistent with this notion, multiple narrow peaks were found to superimpose on the broad trend of the excitation spectrum. As shown in FIG. 10B, the bulk emission spectrum (dark solid line, labeled as "Ensemble") of the nanoparticles revealed a sharp peak at the short wavelength end superimposed on a broad band. The position of the sharp peak depended on the excitation wavelength, which may be indicative of its Raman scattering nature, whereas the broad band was insensitive to the excitation wavelength as expected for fluorescence.

Moreover, as shown in FIG. 10B, the brightness of the nanoparticles allowed their emission spectra (light solid line, labeled as "Single particle") to be recorded at the single-particle level and a moderate level of spectral heterogeneity was observed among the particles.

The Raman peak of each individual nanoparticle can be further resolved into multiple lines. An example shown in inset of FIG. 10B reveals several lines at 936, 1024, 1106, 1433, 1600, 1678, and 1788 $cm^{-1}$, which quantitatively agrees with Raman frequencies for the $CH_2$ deformation, CCN stretching, $NH_2$ rocking, $CH_2$ wagging, $COO^-$ symmetric stretching, $NH_3^+$ asymmetric deformation and NHO stretching of glycine, respectively. Anticipating a small amount of glycine molecules to be present on the 18 nm nanoparticle, the observation of glycine Raman signal from a single nanoparticle suggests a strong Raman enhancement effect due to the silver nanoparticle and the possibility of using the nanoparticles to function as small molecule sensors.

Figure 11A:
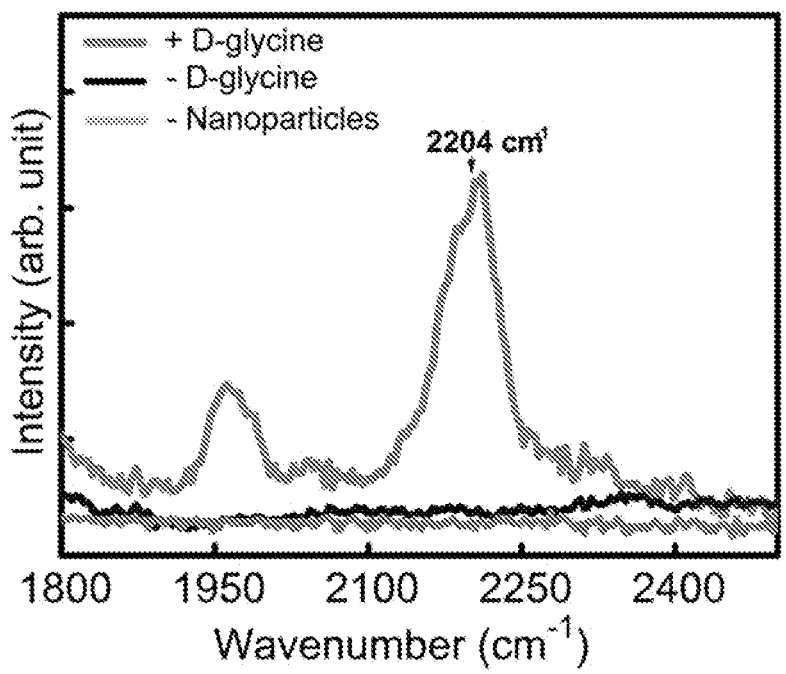
FIG. 11A shows instantaneous Raman spectra from a fluorescent silver nanoparticle before (labeled "-D-glycine") and after (labeled "+D-glycine") addition of 0.4 nM of D-glycine, where the C-D stretching mode is clearly detected after addition of the D-glycine with the presence of the nanoparticles, but is not detected without the presence of the nanoparticles (labeled "-Nanoparticles") in accordance with certain embodiments of the present invention.

To demonstrate the possibility of utilizing these nanoparticles as sensors, the nanoparticles were immersed in low concentrations of deuterated glycine (D-glycine) and the Raman spectra from individual nanoparticles were detected as shown in FIG. 11A. A pronounced C-D vibration line at 2204 cm$^{-1}$ from the D-glycine was observed at sub-nanomolar, and sometimes sub-picomolar, concentrations of the analyte.

Figure 11B:
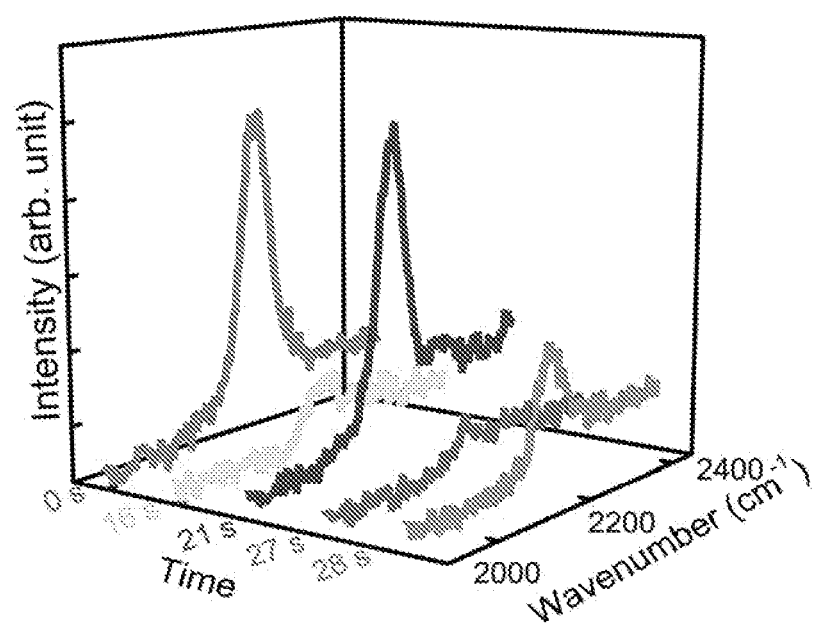
FIG. 11B shows a stochastic on-off (blinking) behavior of the D-glycine Raman signal observed from a single silver nanoparticle in 12 nM D-glycine, where the average signal between 1900 $cm^{-1}$ and 2000 $cm^{-1}$ was subtracted from each trace to remove the background fluorescence signal of the nanoparticle.

As shown in FIG. 11B, the C-D vibration line appeared and disappeared stochastically with time. However, as the concentration of D-glycine increased, the Raman signal was observed continuously in time, suggesting that the observed Raman blinking behavior was due to individual D-glycine molecules approaching and departing from the nanoparticle.

Based on the signal strengths detected from single D-glycine molecules, a Raman cross section can be calculated. The emission intensities (i.e., the number of photons per unit time) of individual silver nanoparticles were about 40 to 50 times larger than that of fluorescent molecule Rhodamine 6G (R6G) molecules under the same excitation conditions. The fluorescence cross section of R6G is believed to be about $2 \times 10^{-16}$ cm$^2$, as described in Du et al., "PhotochemCAD: A computer-aided design and research tool in photochemistry," Photochem Photobiol. Vol. 68, pp. 141-142 (1998). Therefore, the fluorescence cross section of a single silver nanoparticle was estimated to be approximately $10^{-14}$ cm$^2$. Moreover, the Raman scattering signal contained in the C-D vibrational line from single D-glycine molecules was measured to be about 1% of the total emission signal from a single silver nanoparticle. Accordingly, a Raman cross section of a D-glycine molecule in the vicinity of a nanoparticle can be calculated to be about $10^{-16}$ cm$^2$.

Comparing with the typical Raman cross section of small organic molecules ($10^{-31}$-$10^{-30}$ cm$^2$), the enhancement factor due to a silver nanoparticle can be estimated to be on the order of about $10^{14}$-$10^{15}$.

More than 95% of the granular nanoparticles produced by methods in accordance with the present invention exhibited this giant Raman enhancement effect, in contrast to the small percentage (1-3%) observed in previous colloidal silver nanoparticles made from solution-state synthesis.

Figure 12:
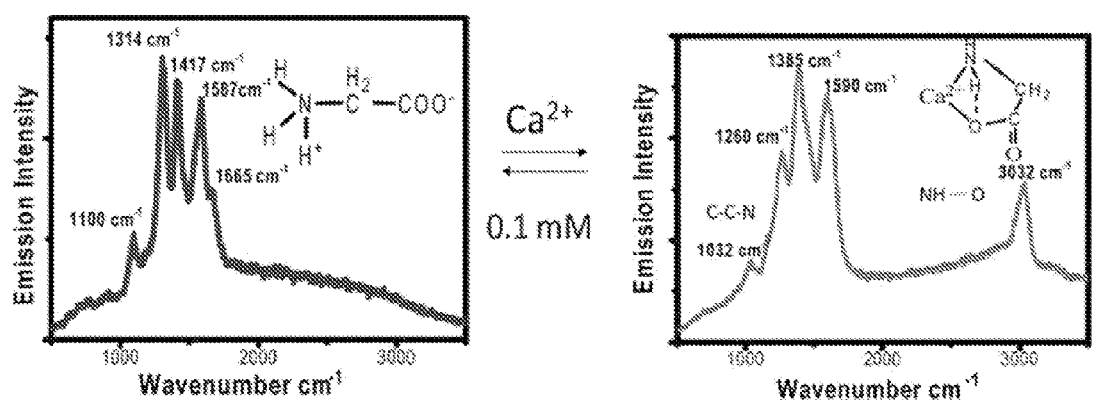
FIG. 12 shows Raman spectra from a fluorescent silver nanoparticle before and after addition of 0.1 mM $CaCl_2$ solution, where a new Raman peak at 3032 $cm^{-1}$ is observed, likely due to the formation of $Ca^{2+}$-glycine complex (HN—HO bond).

In yet another embodiment, fluorescent silver nanoparticles were incubated with 0.1 mM CaCl$_2$ (aqueous) solution, which induced certain changes in the Raman spectra of the silver nanoparticles (see FIG. 12). The new Raman peak at 3032 cm$^{-1}$ likely results from HN—HO bond due to the formation of Ca$^{2+}$-glycine complexes. Accordingly, the Raman emission of fluorescent nanoparticles can be utilized to develop indicators for detection of small ions or molecules.

In yet another embodiment, HS-PEG-SH, HS-PEG-COOH or HS-PEG-NH$_2$ were utilized to coat the fluorescent silver nanoparticles. 40 µl fluorescent silver nanoparticle solution with a concentration of 40 µM was mixed with 1 µl PEG-SH molecule aqueous solution (Mw:5000; 1 mM). After 10 min, solution was centrifuged at 6000 rpm to obtain nanoparticles coated with PEG molecules.

The stability of silver nanoparticles in the different PEG molecules coatings in the different solutions were investigated using a particle analyzer. No aggregation was observed when the particles were dissolved in PBS or NaCl, as well as in pH=1 and pH=13 solutions. The fluorescence property of these nanoparticles was not affected by these coatings. Since these PEG molecules also have functional groups such as SH, NH2, and COOH, these nanoparticles can be further linked to antibodies, specific ligands that can target the proteins or nucleic acids molecules of the live cells.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A nanoparticle comprising:
   a plurality of crystallites within the nanoparticle; wherein
      at least some of the crystallites are about less than 3 nm in size;
      the total number of photons emitted from the nanoparticle upon excitation with an excitation wavelength of the nanoparticle is at least $10^7$,
      the plurality of crystallites are separated from each other by grain boundaries, and
      the nanoparticle comprises about 100 to about 10,000 grain boundaries.

2. The nanoparticle of claim 1, wherein Raman signal for a molecule near the nanoparticle increases at least $10^7$ times.

3. The nanoparticle of claim 1, wherein the total number of photons emitted from the nanoparticle upon excitation with an excitation wavelength of the nanoparticle is at least $10^{11}$.

4. The nanoparticle of claim 3, wherein Raman signal for a molecule near the nanoparticle increases at least $10^{14}$ times.

5. The nanoparticle of claim 1, wherein at least some of the crystallites are about less than 1 nm in size.

6. The nanoparticle of claim 1, wherein at least some of the other crystallites are less than about 10 nm in size.

7. The nanoparticle of claim 5, wherein said at least some of the crystallites having less than 1 nm in size result in discrete energy states that give rise to fluorescent optical transitions.

8. The nanoparticle of claim 1, wherein the nanoparticle has a mean particle diameter of about 1 nm to about 500 nm.

9. The nanoparticle of claim 1, wherein the nanoparticle has a mean particle diameter of about 2 nm to about 20 nm.

10. The nanoparticle of claim 1, wherein the nanoparticle comprises a noble metal.

11. The nanoparticle of claim 1, wherein the nanoparticle comprises a metal and the metal is selected from the group consisting of gold, silver, tantalum, platinum, palladium, rhodium, copper, and mixtures thereof.

12. The nanoparticle of claim 1, wherein the nanoparticle further comprises an organic coating.

13. The nanoparticle of claim 12, wherein the organic coating is selected from the group consisting of glycine, SH-PEG-SH, SH-PEG-COOH, SH-PEG-NH$_2$, and mixtures thereof.

14. The nanoparticle of claim 1, wherein the nanoparticle has a fluorescence cross-section of at least $10^{-14}$ cm$^2$.

15. A composition comprising:
   a plurality of nanoparticles, at least 5% of the plurality of nanoparticle comprising the nanoparticle of claim 1; and
   at least 5% of the plurality of nanoparticles exhibit fluorescence where the total number of photons emitted from each nanoparticle upon excitation with an excitation wavelength of the nanoparticle is at least $10^7$.

16. The composition of claim 15, wherein at least 50% of the plurality of nanoparticles exhibit fluorescence where the total number of photons emitted from each nanoparticle upon excitation with an excitation wavelength of the nanoparticle is at least $10^7$.

17. The composition of claim 15, wherein at least 90% of the plurality of nanoparticles exhibit fluorescence where the total number of photons emitted from each nanoparticle upon excitation with an excitation wavelength of the nanoparticle is at least $10^7$.

18. The composition of claim 15, wherein at least 50% of the plurality of nanoparticles exhibit fluorescence where the total number of photons emitted from each nanoparticle upon excitation with an excitation wavelength of the nanoparticle is at least $10^{11}$.

19. The composition of claim 15, wherein at least 90% of the plurality of nanoparticles exhibit fluorescence where the total number of photons emitted from each nanoparticle upon excitation with an excitation wavelength of the nanoparticle is at least $10^{11}$.

20. The composition of claim 15, wherein at least 5% of the nanoparticles exhibit Raman enhancement where Raman signal for a molecule near an individual nanoparticle in said plurality of nanoparticles increases at least $10^7$ times.

21. The composition of claim 15, wherein at least 50% of the nanoparticles exhibit Raman enhancement where Raman signal for a molecule near an individual nanoparticle in said plurality of nanoparticles increases at least $10^7$ times.

22. The composition of claim 15, wherein at least 90% of the nanoparticles exhibit Raman enhancement where Raman signal for a molecule near an individual nanoparticle in said plurality of nanoparticles increases at least $10^7$ times.

23. The composition of claim 15, wherein at least 5% of the nanoparticles exhibit Raman enhancement where Raman signal for a molecule near an individual nanoparticle in said plurality of nanoparticles increases at least $10^{14}$ times.

24. The composition of claim 15, wherein at least 50% of the nanoparticles exhibit Raman enhancement where Raman signal for a molecule near an individual nanoparticle in said plurality of nanoparticles increases at least $10^{14}$ times.

25. The composition of claim 15, wherein at least 90% of the nanoparticles exhibit Raman enhancement where Raman signal for a molecule near an individual nanoparticle in said plurality of nanoparticles increases at least $10^{14}$ times.

26. The composition of claim 15, wherein each nanoparticle further comprises an organic coating.

27. The nanoparticle of claim 26, wherein the organic coating is selected from the group consisting of glycine, SH-PEG-SH, SH-PEG-COOH, SH-PEG-NH$_2$, and mixtures thereof.

28. A method for producing the nanoparticle claimed in claim 1, the method comprising:
mixing a matrix material with a reactant capable of being thermally reduced to form the nanoparticle, wherein the matrix material has a melting temperature of at least 100° C.;
forming a mixed solid phase comprising the matrix material and the reactant; and
thermally reducing the mixed solid phase to form the nanoparticle of claim 1.

29. The method of claim 28, further comprising:
separating the nanoparticle from the matrix material.

30. The method of claim 29, wherein the separating comprises dissolving the matrix material.

31. The method of claim 28, wherein the thermally reducing is carried out at a temperature where the matrix material is in a solid phase.

32. The method of claim 28, wherein the stoichiometric ratio of the matrix material:the reactant is from about 2:1 to about 50:1.

33. The method of claim 28, wherein the stoichiometric ratio of the matrix material:the reactant is from about 5:1 to about 30:1.

34. The method of claim 28, wherein the stoichiometric ratio of the matrix material:the reactant is from about 15:1 to about 25:1.

35. The method of claim 28, wherein the reactant is a metal ion salt, wherein the metal is selected from the group consisting of copper, gold, silver, tantalum, platinum, palladium, rhodium, and mixtures thereof.

36. The method of claim 28, wherein the matrix material is selected from the group consisting of an organic material, an inorganic material, and salts thereof.

37. The method of claim 36, wherein the matrix material is an the organic material and the organic material is selected from the group consisting of glycine, SH-PEG-SH, SH-PEG-COOH, SH-PEG-NH$_2$, and mixtures thereof.

38. A method for detecting a small molecule, the method comprising:
contacting the small molecule with the nanoparticle of claim 1, and
measuring the Raman signal of the small molecule and the nanoparticle of claim 1.

39. A method for generating photoemission, the method comprising:
exciting the nanoparticle of claim 1 with an electromagnetic radiation capable of generating photons the nanoparticle of claim 1.

40. A fluorescent sensor comprising the nanoparticle of claim 1.

41. A fluorescent biomarker comprising the nanoparticle of claim 1.

42. A Raman sensor comprising the nanoparticle of claim 1.

* * * * *